(12) United States Patent
Korpimäki et al.

(10) Patent No.: US 12,270,811 B2
(45) Date of Patent: Apr. 8, 2025

(54) MICROWELL ASSAY PLATE AND RELATED METHODS

(71) Applicant: WALLAC OY, Turku (FI)

(72) Inventors: Teemu Korpimäki, Turku (FI); Mikko Sairanen, Turku (FI); Ville Veikkolainen, Turku (FI)

(73) Assignee: WALLAC OY, Turku (FI)

( * ) Notice: Subject to any disclaimer, the term of this patent is extended or adjusted under 35 U.S.C. 154(b) by 187 days.

(21) Appl. No.: 17/590,044

(22) Filed: Feb. 1, 2022

(65) Prior Publication Data

US 2022/0244249 A1 Aug. 4, 2022

Related U.S. Application Data

(60) Provisional application No. 63/144,215, filed on Feb. 1, 2021.

(51) Int. Cl.
*G01N 33/543* (2006.01)

(52) U.S. Cl.
CPC . *G01N 33/54366* (2013.01); *G01N 33/54346* (2013.01)

(58) Field of Classification Search
CPC ............... G01N 2333/59; G01N 33/76; G01N 33/54346; G01N 33/54366; G01N 2201/0446; B01L 3/5085; B01L 3/50855; B01L 2300/0829
USPC .......... 422/407, 552, 553; 435/288.4, 288.5; 436/63, 518, 809, 814, 818
See application file for complete search history.

(56) References Cited

U.S. PATENT DOCUMENTS

| 8,721,990 B2 | 5/2014 | Raj et al. |
| 2005/0095697 A1 | 5/2005 | Bachur et al. |
| 2006/0076523 A1 | 4/2006 | Higashiisogawa et al. |
| 2009/0069200 A1 | 3/2009 | Yu |
| 2012/0075626 A1 | 3/2012 | Geva et al. |
| 2014/0273189 A1 | 9/2014 | Ma et al. |

(Continued)

FOREIGN PATENT DOCUMENTS

| WO | 2005029073 A2 | 3/2005 |
| WO | 2007056723 A2 | 5/2007 |
| WO | 2019245744 A1 | 12/2019 |

OTHER PUBLICATIONS

He, Hao, et al. "Quantitative lateral flow strip sensor using highly doped upconversion nanoparticles." Analytical chemistry 90.21 (2018): with Supplemental Information, 17 pages (Year: 2018).*

(Continued)

*Primary Examiner* — Christopher L Chin
(74) *Attorney, Agent, or Firm* — Myers Bigel, P.A.

(57) ABSTRACT

A microplate comprising: a plurality of wells arranged in a two-dimensional array, each of the wells comprising: a bottom surface, sidewalls extending from the bottom surface to form an open top; and at least two subwells in the bottom surface, the at least two subwells having sidewalls that extend below the bottom surface of the well, wherein each of the at least two subwells comprises a capture binding agent that is configured to bind to a target analyte, if present, in a sample. A sample is added to the well such that the sample fluidically contacts each of the at least two subwells such that a target analyte, if present, binds to the capture binding agent in one or more of the at least two subwells.

20 Claims, 3 Drawing Sheets

(56) References Cited

U.S. PATENT DOCUMENTS

| | | |
|---|---|---|
| 2016/0282343 A1 | 9/2016 | Jeyendran et al. |
| 2021/0095235 A1* | 4/2021 | Collins ............. B01L 3/502761 |
| 2021/0364512 A1 | 11/2021 | Sarhan |
| 2021/0364536 A1 | 11/2021 | Busa et al. |

OTHER PUBLICATIONS

Gong, Yan, et al. "A portable and universal upconversion nanoparticle-based lateral flow assay platform for point-of-care testing." Talanta 201 (2019): with Supplemental Information, 15 pages (Year: 2019).*

HCG ELISA Instructions. DRG Instruments GmbH, HCG ELISA EIA-1469, Version 10.0, Dated: Dec. 2020, 36 pages. Downloaded from: https://www.drg-diagnostics.de/files/eia-1469_ifu--hcg_2020-12-17_endeitesfr.pdf (Year: 2020).*

PLGF ELISA Instructions. DRG Instruments GmbH, PLGF ELISA EIA-4529, Version 13.0, Dated: Jul. 2017, 19 pages. Downloaded from: https://www.drg-diagnostics.de/files/eia-4529_ifu--plgf_2017-07-11_ende.pdf (Year: 2017).*

International Search Report and Written Opinion corresponding to PCT/EP2022/052351; Mailed: Sep. 13, 2022, (15 pages).

Invitation to Pay Additional Fees corresponding to PCT/EP2022/052349; Mailed: May 6, 2022 (15 pages).

International Search Report and Written Opinion corresponding to PCT/EP2022/052349; Mailed: Jun. 29, 2022, (19 pages).

Pilavaki, et al., "Optimized Lateral Flow Immunoassay Reader for the Detection of Infectious Diseases in Developing Countries", Sensors, 17(11), 2017, 1-11.

Savyon Diagnostics Ltd., "QuickStripeTM hCG", Product Sheet. Retrieved from: https://www.savyondiagnostics.com/wp-content/uploads/2017/07/QuickStripe_hCG_41110E.V02-09-2017-2.pdf, Jul. 1, 2017, (4 pages).

International Search Report and Written Opinion for PCT/EP2022/052350 mailed May 10, 2022, 18 pages.

He, Hao, et al., "Quantitative Lateral Flow Strip Sensor Using Highly Doped Upconversion Nanoparticles", Anal. Chem. 2018, 90, 12356-12360.

Kazakova, Anna, et al., "Serological Array-in-Well Multiplex Assay Reveals a High Rate of Respiratory Virus Infections and Reinfections in Young Children", MSPHERE, vol. 5, No. 5, Oct. 30, 2019, 14 pages.

Lai, Jinping, et al., "An Upconversion Nanoparticle with Orthogonal Emissions Using Dual NIR Excitations for Controlled Two-Way Photoswitching", Angewandte Chemie International Edition, vol. 53, No. 52, Oct. 27, 2017, pp. 14419-14423.

Magliulo, Maria, et al., "A rapid multiplexed chemilumnescent immunoassay for the detection of *Escheriachia coli* 0157:H7, *Yersinia enterocolitica, Samonella typhimurium,* and *Listeria monocytongenes* pathogen bacteria", Journal of Agricultural and Food Chemistry, American Chemical Society, US, vol. 55, No. 13,Jun. 1, 2017, p. 4933-4939.

Roda, A, et al., "Microtiter format for simultaneous multianalyte detection and development of a PCR-chemiluminescent enzyme for immunoassay for typing human papillomavirus DNAs", Clinical Chemistry, Oxford University Press, US, vol. 48, No. 10 Oct. 1, 2002, pp. 1654-1660.

Li, et al., "Preimplantation Genetic Screening with Spent Culture Medium/Blastocoel Fluid for in Vitro Fertilization", Scientific Reports, 8(9275), 2018, 1-10.

O'Connor, Thomasp., "SNAP Assay Technology", Topics in Companion Animal Medicine, 30(4), 2015, 132-138.

Chen, et al., "A method for the detection of hCG β in spent embryo culture medium based on multicolor fluorescence detection from microfluidic droplets", Biomicrofluidics, 14(2): 024107, 2020, (7 pages).

Scott, et al., "Noninvasive metabolomic profiling of human embryo culture media using Raman spectroscopy predicts embryonic reproductive potential: a prospective blinded pilot study", Fertility and Sterility, 90(1), 2008, 77-83.

* cited by examiner

MICROWELL ASSAY PLATE AND RELATED METHODS

FIELD

The present disclosure relates to a microwell assay plate ("microplates") and related methods, and more particularly to microwell assay plates for reading upconverting nanoparticle signals on and/or in a microwell assay plate.

BACKGROUND

Upconverting nanoparticles (UCNPs) are nanoscale particles (e.g., having a diameter of 1-100 nm) that exhibit photon upconversion in which two or more incident photons of relatively low energy are absorbed and converted into one emitted photon with a higher energy than either of the incident photons. The absorption typically occurs in the infrared range, while emissions typically occur in the visible or ultraviolet regions of the electromagnetic spectrum. UCNPs are typically composed of rare-earth based lanthanide- or actinide-doped transition metals and may be used for a range of applications, including in vivo bio-imaging, bio-sensing, and nanomedicine because of their highly efficient cellular uptake and high optical penetrating power with little background noise in the deep tissue level.

A microplate is a flat plate with multiple wells used for various chemical and biochemical tests. A "standard" microplate typically has 6, 12, 24, 48, 96, 384 or 1536 sample wells arranged in a 2:3 rectangular array. Microplates with 3456 or 9600 wells have also been developed. Microplates are useful for high throughput reactions and/or assays, and in some cases, an "array tape" product has been developed that provides a continuous strip of microplates embossed on a flexible plastic tape. Each well of a microplate typically holds somewhere between tens of nanolitres to several millilitres of liquid. Wells can be either circular or square.

Spatial multiplexing with UCNP labels have been used for printed multiplex microarray immunoassays. See Kazakova, Anna, Laura Kakkola, Henna Päkkilä, Tamara Teros-Jaakkola, Tero Soukka, Ville Peltola, Matti Waris, and Ilkka Julkunen. "Serological Array-in-Well Multiplex Assay Reveals a High Rate of Respiratory Virus Infections and Reinfections in Young Children." MSphere 4, no. 5 (Sep. 11, 2019). Kzazkova et al. uses biotinylated antigens printed in a four by five format on the bottom of streptavidin-coated 96-well microplate wells. UCNPs coated with anti-human IgG are used to detect serum IgG antibodies bound to the array wells.

SUMMARY OF EMBODIMENTS

According to some embodiments, disclosed are methods of detecting a target analyte and/or performing an assay (e.g., a spatial multiplexed assay), where the methods include providing a microplate comprising: a plurality of wells arranged in a two-dimensional array, each of the wells comprising: a bottom surface, sidewalls extending from the bottom surface to form an open top; at least two subwells in the bottom surface, the at least two subwells having sidewalls that extend below the bottom surface of the well, wherein each of the at least two subwells comprises a capture binding agent that is configured to bind to a target analyte, if present, in a sample; adding a sample to the well such that the sample fluidically contacts each of the at least two subwells such that a target analyte, if present, binds to the capture binding agent in one or more of the at least two subwells, wherein an upconverting nanoparticle (UCNP) labeled conjugate in the sample binds with the target analyte, if present; and detecting a label of the upconverting nanoparticle (UCNP) labeled conjugate in one or more of the at least two subwells to thereby determine whether the target analyte is present in the sample.

In some embodiments, the capture binding agent comprises at least a first capture binding agent and a second capture binding agent in different ones of the at least two subwells.

In some embodiments, the UCNP labeled conjugate comprises a first UCNP labeled conjugate and a second UCNP labeled conjugate that are configured to bind to corresponding target analytes bound to the first and second capture binding agents, respectively, in the at least two subwells.

In some embodiments, a UCNP of the first and second UCNP labeled conjugates is the same UCNP, and detecting a label of the labeled conjugate at one or more of the at least two subwells to thereby determine whether the target analyte is present in the sample comprises determining whether first and second target analytes are present based on which of the at least two subwells emit a signal from the UCNP labeled conjugate.

In some embodiments, detecting a UCNP label of the UCNP labeled conjugate at one or more of the at least two subwells comprises impinging photons on the at least two subwells such that the UCNP labeled conjugate emits a signal.

In some embodiments, the methods include determining a concentration of the target analyte based on a signal strength of a signal from the UCNP labeled conjugate, wherein the signal has a signal strength that corresponds to a concentration of the target analyte, if present, in the sample.

In some embodiments, at least one of the first and second capture binding agents comprises a control capture binding agent and the other of the first and second capture binding agents comprises a test capture binding agent, wherein a signal strength of a UCNP labeled conjugate bound to the test capture binding agent relative to a signal strength of a UCNP labeled conjugate bound to the control capture binding agent corresponds to the concentration of the target analyte, if present, in the sample.

In some embodiments, determining the concentration of the target analyte based on the signal strength of the signal from the UCNP labeled conjugate is based on an empirically-based model of actual experience.

In some embodiments, the capture binding agent comprises a first half of a binding pair (e.g., biotin) and the capture binding agent is bound to a surface (e.g., a bottom surface) of the at least two subwells via binding of the first half of the binding pair to a second half of the binding pair (e.g., streptavidin) on the surface of the at least two subwells.

In some embodiments, the upconverting nanoparticle (UCNP) labeled conjugate (e.g., UCNP labeled conjugate) is present on (e.g., dried on) a bottom and/or side of the well prior to adding the sample to the well.

In some embodiments, the method includes adding the upconverting nanoparticle (UCNP) labeled conjugate to the sample.

In some embodiments, the target analyte is human chorionic gonadotropin (hCG) and/or placental growth factor (P1GF).

Also disclosed are microplates that comprise a plurality of wells arranged in a two-dimensional array, each of the wells comprising: a bottom surface, sidewalls extending from the bottom surface to form an open top; at least two subwells in the bottom surface, the at least two subwells having sidewalls that extend below the bottom surface of the well and being sized and configured such that a sample added into the well fluidically contacts each of the at least two subwells, wherein each of the at least two subwells comprises a capture binding agent that is configured to bind to a target analyte, if present, in the sample, which is further configured to bind with an upconverting nanoparticle (UCNP) labeled conjugate in the at least two subwells.

In some embodiments, a UCNP of the first and second UCNP labeled conjugates is the same, and the microplate is configured to be analyzed by a reader that determines whether the first and second target analytes are present based on which of the at least two subwells emit a signal from the UCNP.

In some embodiments, the UCNP labeled conjugate at one or more of the at least two subwells is configured to be detected by impinging photons on the at least two subwells such that the UCNP labeled conjugate emits a signal.

In some embodiments, the microplate is configured such that a concentration of the target analyte is determined based on a signal strength of a signal from the UCNP labeled conjugate, wherein the signal has a signal strength that corresponds to a concentration of the target analyte, if present, in the sample.

BRIEF DESCRIPTION OF THE DRAWINGS

The accompanying drawings, which are incorporated in and constitute a part of the specification, illustrate embodiments of the disclosed microwell assay plates and methods and, together with the description, serve to explain the principles thereof.

DETAILED DESCRIPTION OF EMBODIMENTS

Figure 1:
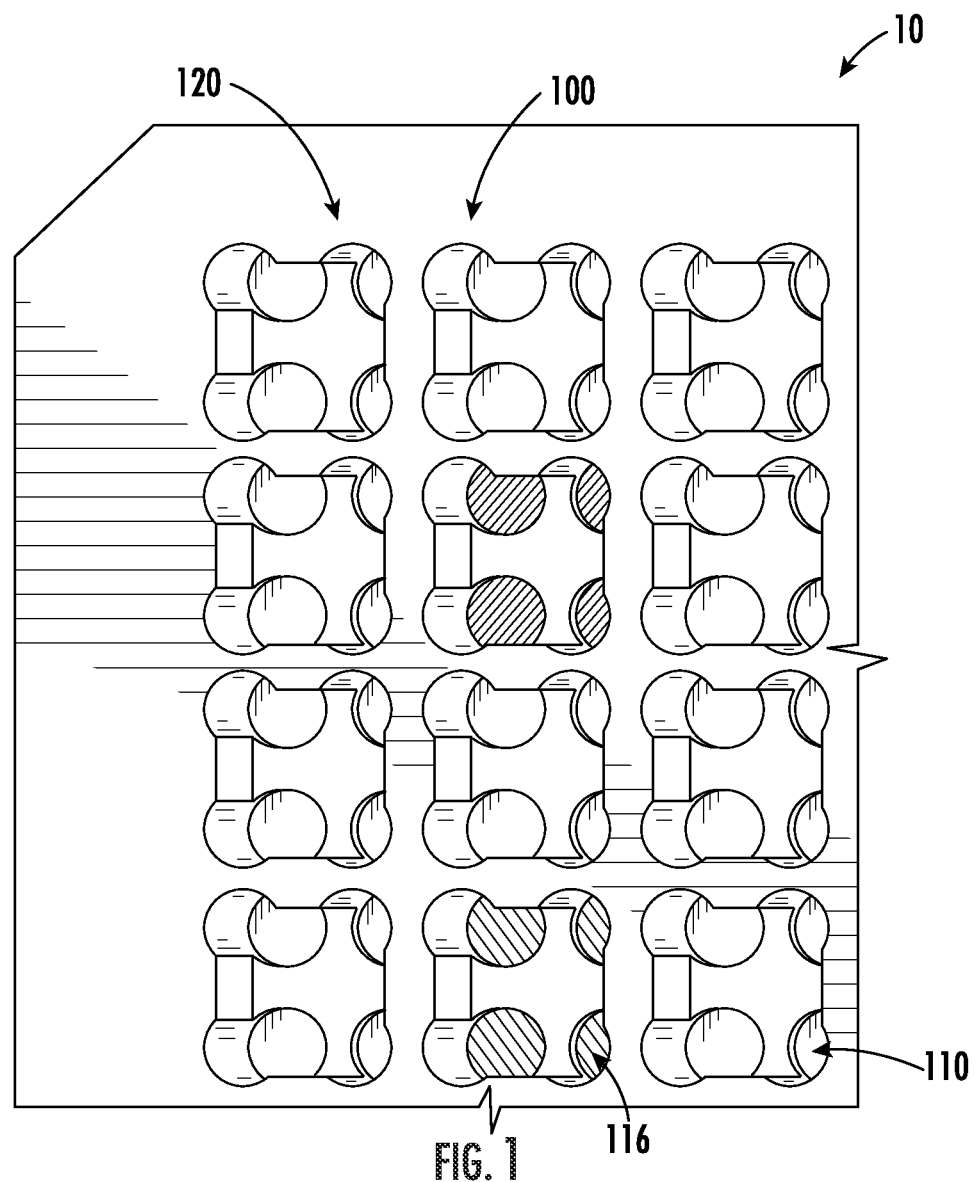
FIG. 1 is a top cut away view of a microwell assay plate according to some embodiments.

The present disclosure now will be described hereinafter with reference to the accompanying drawings and examples, in which embodiments of the disclosed methods and microwell assay plates are shown. These method and microwell assay plates may, however, be embodied in many different forms and should not be construed as limited to the embodiments set forth herein. Rather, these embodiments are provided so that this disclosure will be thorough and complete, and will fully convey the scope of the same to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, processes, actions operations, elements, and/or components, but do not preclude the presence or addition of one or more other features, processes, actions, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations is not limited to the order presented in the claims or figures unless specifically indicated otherwise.

Microplates are used to facilitate many techniques including high-throughput laboratory analysis techniques. Microplates typically include sample holders having a frame and an array of individual sample microwells for holding the samples. A microplate typically has 6, 12, 24, 48, 96, 384 or 1536 sample wells arranged in a 2:3 rectangular array, although microplates with 3456 or 9600 wells have also been developed. Microplates may have standardized sizes that enable the microplate to be used with standard microplate equipment, including handling equipment, washers, and/or readers. The samples can include biological cells and/or chemical agents. In some embodiments, the sample is a bodily fluid such as, but not limited to, placental fluid, cellular fluid, embryonic fluid, blood, blood components, and/or urine. In some embodiments, the sample is an environmental sample such as, but not limited to, a water sample and/or a particulate sample provided in a fluid (e.g., a soil sample provided in water).

Standard microplate readers include upconverting nanoparticle (UCNP) readers that impinge photons on the wells and detect photons emitted by UCNP-labeled conjugates. UCNP detection readers are typically equipped with a laser diode and a sensitive detector to detect signals from UCNPs in a microplate and are compatible with standard microplates. UCNP microplate readers are available from, e.g., UPCON System in Turku, Finland.

A multiplexing array typically includes an array of microwells. In some embodiments, each microwell includes an antigen or capture binding agent, for example, that is biotinylated prior to immobilization on streptavidin-coated well surfaces. Samples, such as serum from a subject, are added to the microwells, for example, to be tested for the presence or absence of target agents (e.g., antibodies) corresponding to the capture binding agents on the wells (e.g., IgG antibodies for different viral antigens). An analyte binding agent or conjugate may comprise a polypeptide such as an antibody or a fragment thereof or an antigen or a fragment thereof. In some embodiments, the signaling agent is attached (e.g., covalently or noncovalently) to the analyte binding agent to form a labeled conjugate. For example, if IgG antibodies for a viral antigen are being detected, the analyte binding agent may be anti-human IgG conjugated onto the signaling agent. In some embodiments, the signaling agent is an upconverting nanoparticle. When the microwell receives the sample, if the target antibody is present, the target antibody binds to the immobilized antigen or capture agent. The labeled conjugate binds to the target antibody. The multiplexing array is typically washed to remove unbound analytes/antigens and signaling agents prior to analysis, which involves detecting the signaling agent at specific locations in various wells. The wells contain a known capture binding agent, and therefore, detection of the signaling agent in a specific well location indicates that the corresponding target analyte is in the sample In some embodiments, the signaling agent of an analyte detecting or binding agent is an upconverting nanoparticle. "Upconverting nanoparticle," "upconversion nanoparticle," and "UCNP" each as used herein refer to a nanoparticle that can or is capable of upconverting two or more incident photons into one photon that has higher energy than either of the two or more incident photons. A "nanoparticle" as used herein refers to a particle having a diameter of at least 1 nm to less than 1000 nm. In some embodiments, an UCNP has a diameter in a range of about 5, 10, 15, 20, 25, 30, 35, 40, or 45 nm to about 50, 55, 60, 65, 70, 75, 80, 85, 90, 95, 100, or 200 nm. In some embodiments, an upconverting nanoparticle can or is capable of converting near-infra-red excitation into visible and/or ultraviolet emission, optionally via a non-linear optical process. For example, an upconverting nanoparticle may absorb infrared (IR) radiation (e.g., near IR radiation) and emit visible and/or ultraviolet radiation, thereby the upconverting nanoparticle can convert a longer radiation wavelength into shorter radiation wavelength. In some embodiments, a UCNP used in a device, system, and/or method of the present disclosure is excited in the near IR region and emits a signal in the visible wavelength range.

A UCNP may comprise a rare-earth element such as a lanthanide (e.g., lanthanum, cerium, praseodymium, neodymium, promethium, samarium, europium, gadolinium, terbium, dysprosium, holmium, erbium, thulium, ytterbium, and/or lutetium) and/or an actinide (e.g., actinium, thorium, protactinium, uranium, *neptunium*, plutonium, americium, curium, berkelium, californium, einsteinium, fermium, mendelevium, nobelium, and/or lawrencium). A rare-earth element may be present in a UCNP in an amount of about 1%, 2%, 4%, or 5% to about 10%, 20%, 30%, 40%, 50%, 60%, 70%, or 80% by weight of the UCNP. In some embodiments, a UCNP is a rare earth doped upconversion nanoparticle such as, but not limited to, a lanthanide-doped UCNP, an actinide-doped UCNP, and any combination thereof. In some embodiments, a UCNP comprises $Er^{3+}$, $Tm^{3+}$, $Y^{3+}$, $La^{3+}$, $Gd^{3+}$, $Sc^+$, $Ca^{2+}$, $Sr^{2+}$, $Ba^{2+}$, $Zr^{4+}$, $Ti^{4+}$, $NaYF_4$, $NaGdF_4$, $LiYF_4$, $YF_3$, $CaF_2$, $Gd_2O_3$, $LaF_3$, $Y_2O_3$, $ZrO_2$, $Y_2O_2S$, $La_2O_2S$, $Y_2BaZnO_5$, $Gd_2BaZnO_5$, and any combination thereof. An exemplary UCNP may be $NaYF_4$:Yb3+, Er3+/Tm3+with 2% Er/20% Yb, 8% Er/60% Yb, 0.5% Tm/20% Yb, or 8% Tm/60% Yb).

A UCNP may be covalently or noncovalently bound to an analyte binding agent to provide a labeled conjugate. In some embodiments, an UCNP is functionalized with a moiety that allows for and/or provides binding of a UCNP to an analyte binding molecule. Such moieties and methods of providing and/or functionalizing UCNPs with such moieties are known in the art. For example, a UCNP may comprise and/or be functionalized with a carboxyl group, an amine (e.g., a primary, secondary and/or tertiary amine) group, a hydroxyl group, thiol group, an amino group, and/or a cyano group, which may be used to bind (e.g., covalently or noncovalently) the UCNP to an analyte binding agent. In some embodiments, a UCNP comprises streptavidin and/or has a streptavidin coating, and an analyte binding agent (e.g., an antibody) is coupled to biotin and to the UCNP via the biotin. In some embodiments, a UCNP is manufactured with a hydrophobic compound and/or layer that can be used to chemically couple, such as via a —COOH group, an analyte binding agent (e.g., an antibody) to the UCNP. In some embodiments, an analyte binding agent is an antibody or a fragment thereof and a UCNP is bound to the antibody or fragment thereof, optionally via a covalent bond. In some embodiments, a UCNP comprises silica (e.g., a silica layer and/or an amorphous silica shell) that is optionally around the UCNP. In some embodiments, a UCNP comprises a polyanion such as poly(styrene sulfonate), a polycation such as poly(allylamine hydrochloride), a polyacrylic acid (PAA), a polyethylene glycol (PEG), and/or a copolymer thereof and/or any combination thereof, each of which may optionally be in the form of a coating (e.g., having a thickness of about 1 nm to about 5, 10, 15, or 20, nm) around the UCNP.

In some embodiments, using a labeled conjugate comprising a UCNP may provide advantages for an assay and/or detection in a microplate. For example, a labeled conjugate comprising a UCNP may reduce or avoid non-specific binding. Thus, a non-specific binding signal may be reduced or avoided.

Figure 2:
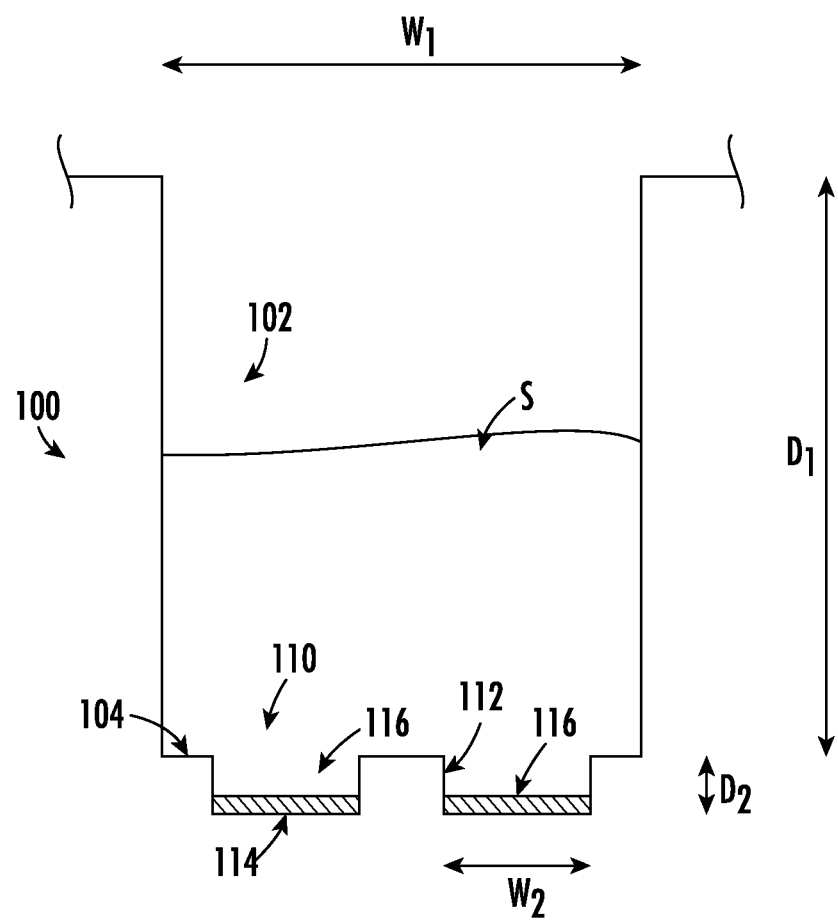
FIG. 2 is a cross sectional view of a microwell of the microwell assay plate of FIG. 1 having subwells on the bottom surface of the microwell.

As shown in FIGS. 1-2, a microplate 10 according to some embodiments includes a plurality of wells 100 arranged in a two-dimensional array 120. The wells 100 include a sidewall 102 and a bottom surface 104. The sidewall 102 extends from the bottom surface 104 to form an opening, and at least two subwells 110 are formed on the bottom surface 104. The subwells 110 have a subwell sidewall 112 and a subwell bottom surface 114. The subwell sidewall 112 extends below the bottom surface 104 of the well 100 and is sized and configured such that a sample S added to the well bottom surface 104 fluidically contacts the at least two subwells 110 formed in the bottom surface 104 of that well 100.

As shown in FIG. 2, the subwells 110 have a capture binding agent 116 thereon that is configured to bind to a target analyte, if present, in a sample S. A labeled conjugate may be in contact with and/or be bound to the target analyte to provide a labeled target analyte in the subwells 110 such that detection of the labeled target analyte in a respective subwell 110 may be used to determine if the target analyte is present in the sample S. In some embodiments, the capture binding agent 116 comprises a first half of a binding pair and the capture binding agent 116 is bound to a surface of the subwells 110 via binding of the first half of the binding pair to a second half of the binding pair on the surface of the subwells 110.

One or more subwell(s) 110 of the well 100 may comprise the same or different capture binding agents 116 that are configured to bind to the same or different target analytes in a sample S.

In the FIGS. 1-2 embodiments, each well 100 includes four subwells 110; however, it should be understood that a well with any suitable number of subwells 110 may be used. In some embodiments, as shown in FIG. 1, a "standard" microplate may be modified such that selected portions of the standard well walls are removed and the standard wells are joined together to form a larger "super" well, such as well 100, and the standard wells are the subwells 110 of the super well. For example, in some embodiments, a standard 384-well plate may be modified so that each 2×2 grouping of four standard wells is combined to form a single (super) well comprising four standard wells as subwells, thereby creating 96 such (super) wells, each (super) well having four subwells 110. In some embodiments, each well of the standard microwell plate becomes a subwell of a "super" well, while in other embodiments, only certain groupings of the standard microwell plate become subwells, while other wells may remain in their standard configuration. In such embodiments, the positioning of the original e.g., 384, wells has not changed, yet rather, only the grouping of such wells into subwells, as described herein. Accordingly, standard microplate readers capable of reading, e.g., 384 well microplates, may be used to analyze signals of the subwells 110. Such techniques are merely illustrative, however, and microplates according to embodiments of the present disclosure may be manufactured according to any suitable technique. In some embodiments, one or more respective well(s) of a standard 6, 12, 24, 48, 96, 384, 536, 3456 or 9600 well microplate may include 2, 3, 4, 5, 6, 7, 8, or more subwells. For example, a bottom surface of a well may be divided up, partitioned, and/or formed to comprise two or more subwells that may include the same or a different capture binding agent.

As illustrated in FIG. 2, the wells 100 have a width $W_1$ and the sidewalls 102 have a depth $D_1$. The subwells 110 have a width $W_2$ and the subwell sidewalls 112 have a depth $D_2$. In some embodiments, the subwells 110 have width $W_2$ and/or a sidewall depth $D_2$ that is sufficient to encapsulate and/or comprise the capture binding agents 116 and optionally allow for separation of the capture binding agents 116 of each respective subwell 110 from each other, while also allowing (fluidic) contact and/or access of the sample S to all of the subwells 110. In some embodiments, the depth $D_1$ of the sidewall 102 is about 9 mm and the depth $D_2$ of the subwell sidewall 112 is about 1 mm. However, the depth $D_1$ of the sidewall 102 can be about 4, 5, 6, 7, 8 or 9 mm to about 10, 11, 12, 13, 14, 15 mm or more and the depth $D_2$ of the subwell sidewall 112 can be about 0.5, 0.75, 1.0 mm to about 1.25, 1.5, 1.75 mm or more. In some embodiments, the width $W_1$ of the well 100 is about 85.47, 85.48 or 85.6 mm; however, the width $W_1$ of the well 100 may be about 50, 60, 70, 80, 90 mm to about 100, 110, 120, 130, 140 mm or more. The width $W_2$ of the subwell 110 may be about 10, 15, 20, 25, 30, 35, 40, 45 mm to about 50, 55, 60, 65, 70, 75, 80, 85, 90 mm or more. In some embodiments, the subwell sidewall 112 depth $D_2$ is about 5%-50% of the depth $D_1$ of the well sidewall 102.

When a sample S is added to the well 100, the sample S contacts each of the subwells 110 and the corresponding capture binding agent 116 in each subwell 110. Therefore, a single sample S can be tested for two or more target analytes in a well 100 by simultaneously contacting different capture binding agents 116 present in different subwells 110.

The capture binding agent 116 may be immobilized antigens or capture agents, such as biotinylated antigens that may be immobilized onto streptavidin-coated surfaces on the bottom of the subwells 110. In some embodiments, the same label may be used for different target analytes such that the presence or absence of the target analyte may be determined based on the location of the detected signal.

A sample S may be added to the well 100 such that the sample S fluidically contacts all of the subwells 110 such that a target analyte, if present, binds to the capture binding agent 116 in one or more of the subwells 110. A labeled conjugate may be in contact with the sample S such that the labeled conjugate binds with the at least one target analyte, if present. In some embodiments, a labeled conjugate may be combined with the sample S prior to adding the sample S to the well 100 such that the sample S includes the labeled conjugate and the labeled conjugate may be pre-incubated with the sample S for a period of time prior to adding the sample S to the well 100. In some embodiments, a labeled conjugate may be added into the well 100 (and/or subwells 110) prior to and/or after adding the sample S to the well 100 (and subwells 110). Typically, the sample S is removed from the wells 100 (and subwells 110) after a period of time in the presence of the labeled conjugate in the wells 100 (and/or subwells 110) and/or the wells 100 (and subwells 110) are washed after a period of time in the presence of the labeled conjugate in the wells 100 (and subwells 110) to remove unbound labeled conjugates. The label of the labeled conjugate in the subwells 110 is detected, if present, to thereby determine whether the predetermined target analyte is present in the sample based on an identified subwell 110 having detectable labels thereon, for example, using commercially available microplate readers.

The concentration of a capture binding agent 116 in a subwell 110 may be sufficient to provide a detectable signal when bound to a labeled conjugate and/or sufficient to be above background noise and/or signal.

In some embodiments, a well 100 comprises two or more (e.g., 2, 3, 4, 5, or more) capture binding agents 116, with different capture binding agents 116 in different ones of the subwells 110 of a respective well 100. In this configuration, each of the subwells 110 may allow for the detection of different target analytes in the same sample S in a single well 100 using the different capture binding agents in corresponding subwells 110. In embodiments, the label used in different subwells 110 of a well 100 may be the same; however, the different target analytes may be detected based on the position of the subwell 110 and the known antigen capture binding agent in the each of the subwells 110. The subwell locations or positions in which signals are detected indicate a presence or absence of the corresponding target analyte in the sample S.

As noted, the labeled conjugate may be an agent bound to a UCNP such as a UCNP labeled antibody(e.g., human IgG-coated UCNPs). The UCNP labeled antibody may be configured to bind to a target analyte that may be present in a sample S and/or bound to a capture binding agent 116 in a subwell 110. The UCNP labeled antibody may be detected by impinging photons on the subwells 110 such that the UCNP of the UCNP labeled antibody emits a signal, which may be detected by an imager. The resulting detection image may indicate one or more target analyte(s) are in the sample S based on which subwells 110 emit signals indicating a presence of a target analyte corresponding to the predetermined antigen capture binding agent 116 in the subwell 110. In some embodiments, two or more (e.g., 2, 3, 4, 5, or more) different labeled analyte binding agents or conjugates may be used to detect different target analytes at different subwells 110. In some embodiments, the labeled conjugate may be added directly to the well 100, dried on a bottom and/or sidewall of the well 100 or subwell 110, added directly to the fluid sample S, and/or provided on and/or in a conjugate pad in the well 100 or one or more of the subwells 110.

In some embodiments, a concentration of the target analyte may be determined based on a signal strength of the signal. The signal has a signal strength that corresponds to a concentration of the target analyte, if present, in the sample S, e.g., such that a higher signal strength indicates a higher target analyte concentration. The correlation between the target analyte concentration and signal strength may be determined experimentally by detecting signal strengths at one or more known target analyte sample concentrations. It should be understood by one of skill in the art that the signal strength may also be dependent on other factors, which may be controlled for consistency and accuracy, such as temperature, time of analyte exposure to the binding agent, and the like.

In some embodiments, the disclosed methods provide a limit of detection for the target analyte of less than 25 mIU/mL, such as less than 20, 15, 10, 5, 1, 0.5 or 0.3 mIU/mL. In some embodiments, the disclosed methods provide a limit of detection for the target analyte of about 0.1 or 0.2 mIU/mL to about 0.3, 0.5, or 1 mIU/mL.

In some embodiments, a fluid sample S and labeled conjugate may be contacted (e.g., fluidically contacted, combined and/or mixed together) prior to or at the same time that the fluid sample S is added to the well 100. The labeled conjugate may be added into the fluid sample and the fluid sample S comprising the labeled conjugate may then be added to the well 100 (or vice versa) and contacted with an antigen capture binding agent 116 in the subwells 110. The sample S may therefore include additional components, such as the labeled conjugate. For example, the labeled conjugate may be released from a surface of the well 100 or subwell 110 and/or may be dissolved and/or suspended in the sample S before and/or after the sample S is added to the well 100/subwell 110. In the fluid sample S, the labeled conjugate may bind with a target analyte (e.g., an analyte of interest), if present, in the fluid sample S. The sample S may also be an undiluted fluid or the sample S may be diluted such as with a buffer or diluting liquid (e.g., water, saline, etc.).

In some embodiments, the capture binding agents may include a control capture binding agent and a test capture binding agent. The immobilized control binding agent may bind to a control agent and/or the analyte binding agent. The signal strength of a UCNP labeled antibody bound to the test capture binding agent relative to a signal strength of a UCNP labeled antibody bound to the control capture binding agent may correspond to the concentration of the target analyte, if present, in the sample.

Embodiments according to the present disclosure will now be described according to the following non-limiting example.

EXAMPLE

A 384-well plate was modified so that each 2×2 grouping of four wells were combined to form four subwells of a single "super" well, thereby creating a 96-(super)well plate with four subwells in the bottom of each (super) well. The bottom of the four subwells can be coated with different capture antibodies configured to bind an analyte and using laser excitation, e.g., with UCNP labels, location-specific signal measurements can be performed to identify which target analytes are present in a sample.

This method allows multiplexing (e.g., multiple analytes from a single well and single sample) using a single label as the antibodies are localized in each subwell. In some embodiments, existing microwell plate formats/standards may be utilized, such as 384—and 96-well plates, such that compatibility with existing manufacturing lines and measurement devices/instruments may be achieved.

Figure 3:
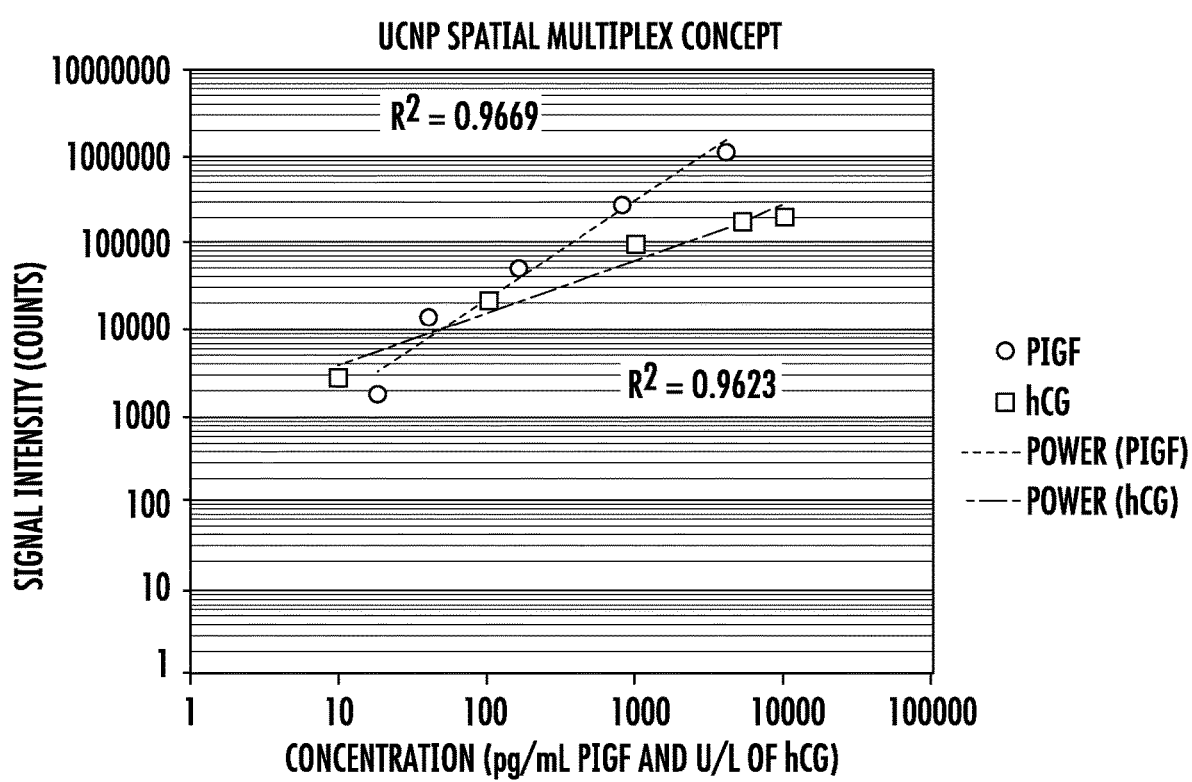
FIG. 3 is a graph showing upconverting nanoparticle (UCNP) spatial multiplex concentration measurements for PlGF and hCG as a function of detected photon counts in the microwell assay plate of FIG. 1 according to some embodiments.

In this example, placental growth factor ("P1GF") and human chorionic gonadotropin("hCG") were coated in alternate subwells so that there were two spots/subwells for P1GF and two spots/subwells for hCG within one (super) well. Detection antibodies or analyte binding agents with the same label (e.g., labeled UCNP conjugates) were mixed and used to measure samples including various levels of P1GF and hCG as shown in FIG. 3. Accordingly, the concentration of a target analyte, such as PlGF and hCG, was detected in a sample, for example, using a signal strength of known concentrations as a reference. When two or more subwells utilize the same antigen capture binding agent to detect the same target analyte, the signal strength may be averaged to increase the accuracy of the measurement.

In some embodiments, the method provides a limit of detection for the target analyte (e.g., human chorionic gonadotropin (hCG)) of less than 25, 10, 1, 0.5 or 0.3 mIU/mL, optionally wherein the method provides a limit of detection for the target analyte (e.g., human chorionic gonadotropin (hCG)) of about 0.1 or 0.2 mIU/mL to about 0.3, 0.5, or 1 mIU/mL.

In some embodiments, a function and/or viability of an in vitro embryo (e.g., an in-vitro fertilization (INT) embryo) may be evaluated and/or monitored according to some embodiments of the present disclosure. For example, a function and/or viability of an in vitro embryo may be evaluated, monitored and/or estimated by detecting the presence of a target analyte and/or determining an amount of a target analyte (e.g., a viability associated marker) in a fluid sample comprising culture media in which the in vitro embryo was cultured using various microplates discussed herein.

Currently, in vitro embryos are evaluated morphologically by visual inspection to evaluate function and/or viability of the in vitro embryo such as by monitoring cell division and/or counting the number of cells in an embryo. The microplate technology using UCNP detection labels as described herein can be used evaluate the function and/or viability of in vitro embryos such as IVF embryos. In some embodiments, an in vitro embryo is grown on and/or in a cell culture container (e.g., a cell culture dish), optionally non-invasively. In some embodiments, the in vitro embryo is grown and/or cultured at a controlled temperature and/or in an incubator.

Accordingly, disclosed are methods of evaluating and/or monitoring function and/or viability of an embryo grown in vitro, such methods comprising adding a fluid sample comprising culture media in which the embryo was cultured to the microplates described herein, wherein the fluid sample contacts a labeled conjugate that binds to a target analyte, when present in the fluid sample, and the microplate includes subwells with capture agents corresponding to the viability marker target analytes and, when the target analyte is present; and detecting a signal at the subwell, wherein the signal indicates the presence of the target analyte. In some embodiments, the methods provide a limit of detection for the target analyte of less than 25 mIU/mL, such as less than 20, 15, 10, 5, 1, 0.5 or 0.3 mIU/mL. In some embodiments, the methods provide a limit of detection for the target analyte of about 0.1 or 0.2 mIU/mL to about 0.3, 0.5, or 1 mIU/mL. The fluid sample may be or comprise culture media in which the in vitro embryo was cultured (e.g., grown). Typically, after fertilization of an embryo in vitro, the embryo is cultured in culture media for a given time period and the culture media may be changed one or more times (e.g., 2, 3, 4, or more times) during this given time period. For example, the day the in vitro embryo is fertilization is day 0, and the in vitro embryo may be cultured for 1, 2, 3, 4, 5, 6, 7, 8, 9, or more days after fertilization (i.e., day 1, 2, 3, 4, 5, 6, 7, 8, 9, etc. after fertilization). In some embodiments, the culture media is changed every day or every two, three, or more days after day 0. In some embodiments, all or a portion of the fluid sample comprises culture media from day 1, 2, 3, 4, 5, 6, 7, 8, or 9 after fertilization of the in vitro embryo. In some embodiments, the fluid sample comprises culture media in which the embryo was cultured at day 4, 5, or 6 after fertilization (day 0). The fluid sample may comprise all or a portion of the culture media in which the in vitro embryo was grown. In some embodiments, the fluid sample comprises and/or is about 1, 5, 10, or 20 μL to about 30, 40, 50, 60, 70, 80, 90, or 100 μL of culture media in which the embryo was cultured, optionally on a particular day (e.g., at day 4, 5, or 6 after fertilization). In some embodiments, the fluid sample comprises and/or is about 1 μL to about 50 μL of culture media in which the embryo was cultured, optionally on a particular day (e.g., at day 4, 5, or 6 after fertilization). One or more target analytes may be present in the fluid sample. A target analyte may be secreted by an in vitro embryo into culture media in which the embryo is present and detected in a method as described herein.

A method of the present disclosure may comprise evaluating and/or monitoring function and/or viability of an embryo cultured in vitro at two or more different times after fertilization (day 0) of the embryo. For example, the method may comprise evaluating samples from first and second culture media using the microplates described herein, wherein the first and second culture media are obtained from different days after fertilization of the embryo. The first culture media may be culture media in which the embryo was grown on day 4 after fertilization and the second culture media may be culture media in which the embryo was grown on day 6 after fertilization. In some embodiments, the first and second signals from the subwells may be compared. In some embodiments, the first and second signals may be quantified to determine the amount of the target analyte in the first culture media and/or second culture media.

A method of the present disclosure may be performed in less than 30 minutes. In some embodiments, the method is performed in about 1, 5, or 10 minute(s) to about 15, 20, 25, or 30 minutes.

In some embodiments, the target analyte is human chorionic gonadotropin (hCG) and/or placental growth factor (P1GF).

A function and/or predicted viability of an in vitro embryo may be based on an empirically-based model of actual clinical experience. In some embodiments, the empirically-based model of actual clinical experience may include tests in which the concentration of the target analyte is known. The concentration of the target analyte in a sample with an unknown concentration may be determined based on a mathematical model, such as a linear regression model. In some embodiments, the empirically-based model of actual clinical experience may include viability measurements or other data based on the clinically-observed viability of embryos with a known concentration of the target analyte.

Accordingly, in some embodiments, a signal intensity of a subwell in a microplate described herein may indicate an amount of the target analyte to thereby predict a function and/or viability of an in vitro embryo. Therefore, a function and/or viability of an in vitro embryo may be determined using a microplate assay. In some embodiments, the method further comprises visually evaluating the morphology of the embryo such as visually evaluating cell division of the embryo and/or the number of cells in the embryo. The visual evaluation may be performed using microscopy. The morphological information may be compared to signals obtained from a microplate to evaluate and/or determine a function, stage, and/or viability of the embryo.

The foregoing is illustrative of the present disclosure and is not to be construed as limiting thereof. Although a few exemplary embodiments have been described, those skilled in the art will readily appreciate that many modifications are possible in the exemplary embodiments without materially departing from the novel teachings and advantages of this disclosure. Accordingly, all such modifications are intended to be included within the scope of the invention as defined by the claims. Therefore, it is to be understood that the foregoing disclosure is illustrative and is not to be construed as limited by the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of detecting a target analyte and/or performing a spatial multiplexed assay, the method comprising:
   providing a microplate comprising:
   a plurality of wells arranged in a two-dimensional array, each of the wells comprising:
   a bottom surface,
   sidewalls extending from the bottom surface to form an open top;
   at least two subwells in the bottom surface, the at least two subwells having sidewalls that extend below the bottom surface of the well, wherein each of the at least two subwells comprises a capture binding agent that is configured to bind to a target analyte, if present, in a sample;

adding a sample to the well such that the sample fluidically contacts each of the at least two subwells such that a target analyte comprising human chorionic gonadotropin (hCG) or placental growth factor (PIGF), if present, binds to the capture binding agent in one or more of the at least two subwells, wherein an upconverting nanoparticle (UCNP) labeled conjugate in the sample binds with the target analyte, if present; and detecting a label of the upconverting nanoparticle (UCNP) labeled conjugate at one or more of the at least two subwells to thereby determine whether the target analyte is present in the sample.

2. The method of claim 1, wherein the capture binding agent comprises at least a first capture binding agent and a second capture binding agent in different ones of the at least two subwells.

3. The method of claim 2, wherein the UCNP labeled conjugate comprises a first UCNP labeled conjugate and a second UCNP labeled conjugate that are configured to bind to corresponding target analytes bound to the first and second capture binding agents, respectively, in the at least two subwells.

4. The method of claim 3, wherein a UCNP of the first and second UCNP labeled conjugates is the same UCNP, and detecting a label of the labeled conjugate at one or more of the at least two subwells to thereby determine whether the target analyte is present in the sample comprises determining whether first and second target analytes are present based on which of the at least two subwells emit a signal from the UCNP labeled conjugate.

5. The method of claim 4, wherein detecting a UCNP label of the UCNP labeled conjugate at one or more of the at least two subwells comprises impinging photons on the at least two subwells such that the UCNP labeled conjugate emits a signal.

6. The method of claim 5, further comprising determining a concentration of the target analyte based on a signal strength of a signal from the UCNP labeled conjugate, wherein the signal has a signal strength that corresponds to a concentration of the target analyte, if present, in the sample.

7. The method of claim 6, wherein at least one of the first and second capture binding agents comprises a control capture binding agent and other of the first and second capture binding agents comprises a test capture binding agent, wherein a signal strength of a UCNP labeled conjugate bound to the test capture binding agent relative to a signal strength of a UCNP labeled conjugate bound to the control capture binding agent corresponds to the concentration of the target analyte, if present, in the sample.

8. The method of claim 6, wherein determining the concentration of the target analyte based on the signal strength of the signal from the UCNP labeled conjugate is based on an empirically-based model of actual experience.

9. The method of claim 1, wherein the capture binding agent comprises a first half of a binding pair and the capture binding agent is bound to a surface of the at least two subwells via binding of the first half of the binding pair to a second half of the binding pair on the surface of the at least two subwells.

10. The method of claim 1, wherein the upconverting nanoparticle (UCNP) labeled conjugate is present on a bottom and/or side of the well prior to adding the sample to the well.

11. The method of claim 1, further comprising adding the upconverting nanoparticle (UCNP) labeled conjugate to the sample.

12. The method of claim 1, wherein the target analyte is human chorionic gonadotropin (hCG) and the sample comprises a culture media in which an embryo is cultured.

13. The method of claim 1, wherein the target analyte is placental growth factor (PIGF) and the sample comprises a culture media in which an embryo is cultured.

14. A method of detecting a target analyte and/or performing a spatial multiplexed assay, the method comprising:
providing a microplate comprising:
a plurality of wells arranged in a two-dimensional array, each of the wells comprising:
a bottom surface,
sidewalls extending from the bottom surface to form an open top;
at least two subwells in the bottom surface, the at least two subwells having sidewalls that extend below the bottom surface of the well, wherein each of the at least two subwells comprises a capture binding agent that is configured to bind to a target analyte, if present, in a sample, wherein the target analyte comprises human chorionic gonadotropin (hCG);
adding a sample to the well such that the sample fluidically contacts each of the at least two subwells such that a target analyte, if present, binds to the capture binding agent in one or more of the at least two subwells, wherein an upconverting nanoparticle (UCNP) labeled conjugate in the sample binds with the target analyte, if present, wherein the sample comprises a culture media in which an in vitro embryo is cultured;
detecting a label of the upconverting nanoparticle (UCNP) labeled conjugate at one or more of the at least two subwells to thereby detect the target analyte comprising hCG in the sample; and
evaluating the in vitro embryo based on the detection of the target analyte comprising hCG in the sample comprising the culture media in which the in vitro embryo is cultured.

15. The method of claim 14, wherein the sample media comprises between 1 and 100 µL of culture media in which the embryo was cultured.

16. The method of claim 14, wherein detecting the label of the upconverting nanoparticle (UCNP) labeled conjugate at one or more of the at least two subwells to thereby detect the target analyte comprising hCG comprises detecting a concentration of hCG at a limit of detection of less than 25 mIU/mL.

17. The method of claim 14, wherein the target analyte comprises human chorionic gonadotropin (hCG) is a first target analyte in a first one of the at least two subwells, wherein a second target analyte in a second one of the at least two subwells comprises placental growth factor ("PIFG"), and evaluating the in vitro embryo further comprises evaluating the in vitro embryo based on the detection of the first target analyte comprising hCG in the sample and the second target analyte comprising PIFG comprising the culture media in which the in vitro embryo is cultured.

18. The method of claim 14, wherein evaluating the in vitro embryo comprises evaluating samples from first and second culture media.

19. The method of claim 18, wherein the first and second culture media are obtained from different days after fertilization of the embryo.

20. The method of claim 14, wherein evaluating the in vitro embryo comprises comparing a signal strength of the label with an unknown concentration of target analyte with the signal strength(s) of the label in reference sample(s) with a known concentration of the target analyte.

\* \* \* \* \*